United States Patent
Alisi et al.

[11] Patent Number: 5,424,451
[45] Date of Patent: Jun. 13, 1995

[54] PROCESS FOR PREPARING AMINOALKYLCARBAMIC ESTERS OF ESEROLINE

[75] Inventors: Maria A. Alisi, Rome; Mario Brufani, Castelgandolfo; Maria C. Cesta, Rome; Luigi Eieocamo, Rome; Gianluca Gostoli, Rome; Sperandina Lappa, Rome; Pier Giuseppe Pagella, Catraglia; Enrico Ferrari, Giovanni; Stefano Maiorana, Milan; Donata Marchesini, Milan, all of Italy

[73] Assignee: Mediolanum Farmaceutici S.p.A., Milan, Italy

[21] Appl. No.: 177,325

[22] Filed: Jan. 4, 1994

Related U.S. Application Data

[62] Division of Ser. No. 79,921, Jun. 23, 1993, Pat. No. 5,302,593.

[30] Foreign Application Priority Data

Jun. 25, 1992 [IT] Italy .................. MI92A1559

[51] Int. Cl.$^6$ ............ A61K 31/40; C07D 209/58
[52] U.S. Cl. ................. 548/429; 544/58.5; 544/142; 544/372; 546/19; 546/199
[58] Field of Search ............ 548/429; 514/411

[56] References Cited

FOREIGN PATENT DOCUMENTS 253372 1/1988 European Pat. Off.
513703 11/1992 European Pat. Off.

Primary Examiner—Robert W. Ramsuer
Attorney, Agent, or Firm—Oliff & Berridge

[57] ABSTRACT

Aminoalkylcarbamic esters of eseroline suitable for use as cholinesterase activity inhibitors, having general formula (I)

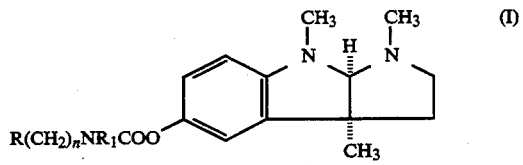

where R stands for an amine selected out of the group consisting of

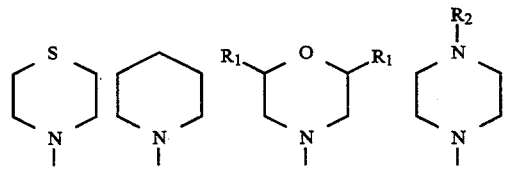

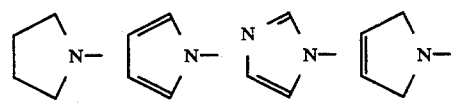

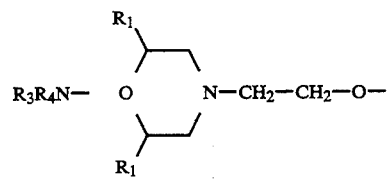

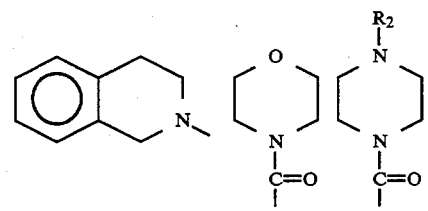

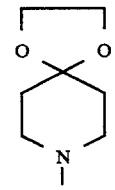

and n, R1, R2, R3, and R4 are as defined in the text.

7 Claims, No Drawings

PROCESS FOR PREPARING AMINOALKYLCARBAMIC ESTERS OF ESEROLINE

This is a Division of application Ser. No. 08/079,921, filed Jun. 23, 1993, now U.S. Pat. No. 5,302,593.

PRIOR ART

Several memory dysfunctions, and in particular the senile dementia of Alzheimer's type, are characterized by a reduction in the acetylcholine neurotransmitter levels in some areas of brain. In these cases, the inhibition of acetylcholinesterase, an enzyme that hydrolyzes acetylcholine, is therapeutically effective.

As known, physostigmine is a potent natural inhibitor of acetylcholinesterase which, as demonstrated by several clinical tests, has beneficial effects on patients affected by mental diseases. However, its unfavourable pharmacokinetic properties and side effects make its clinical use scarcely advisable.

As also known, heptastigmine, or heptylcarbamic ester of eseroline, is a less potent acetylcholinesterase inhibitor than physostigmine, but shows better pharmacokinetic properties and reduced side effects. Heptastigmine gave good results in a clinical pilot test on patients affected by Alzheimer's disease. However, it caused neutropenia phenomena in some, though very few, patients.

Further derivatives of eseroline were synthesized in recent times. For example, a compound consisting of eseroline carbamic ester with morpholine was disclosed in Example 30 of EPA 0253372 by Hoechst-Roussel. However, said compound produced a low acetylcholinesterase activity depression and was not further developed.

SUMMARY

It has now been surprisingly found that the compounds as per formula (I) have none of the disadvantages of the compounds already known and exhibit a high inhibition of cholinesterase activity.

The present invention relates to aminoalkylcarbamic esters of eseroline as per general formula (I)

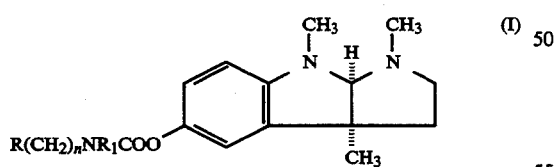

where n is an integer from 2 to 20; R1 may be H, methyl, ethyl, propyl, and isopropyl; and R is an amine selected out of the group consisting of

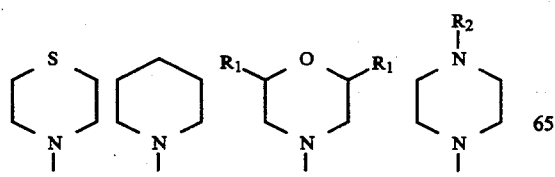

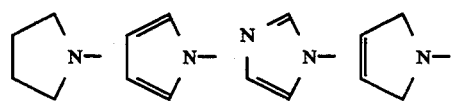

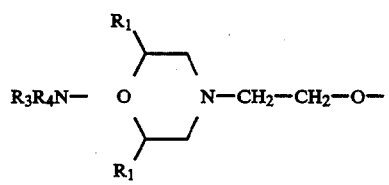

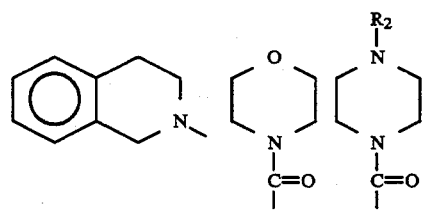

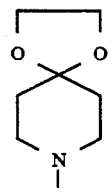

where R2 is linear or branched $C_1$-$C_4$ alkyl, or acyl or benzyl; R3 and R4 are linear or branched $C_1$-$C_4$ alkyls, or benzyl or methoxyethyl, methoxypropyl, methoxybutyl.

The raw material used for the preparation of the esters according to the present invention is eseroline (II)

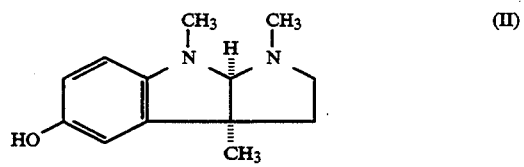

hereinafter also referred to as ESOH. The relative preparation process is characterized by the following steps:

a) heterocyclic compound RH, where R is as defined above, is caused to react with Ω-haloalkylphthalimide as per formula (III)

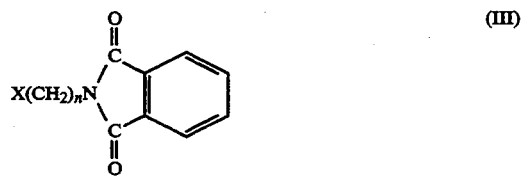

where X is selected out of the group consisting of F, Cl, Br, and I;

b) the phthalic group of the obtained compound is removed by hydrazinolysis to form a primary amino derivative as per formula (IV)

$$R(CH_2)_nNH_2 \quad (IV)$$

c) carbonyl diimidazole is caused to react first with eseroline and then with the aforesaid amino derivative according to the following reactions:

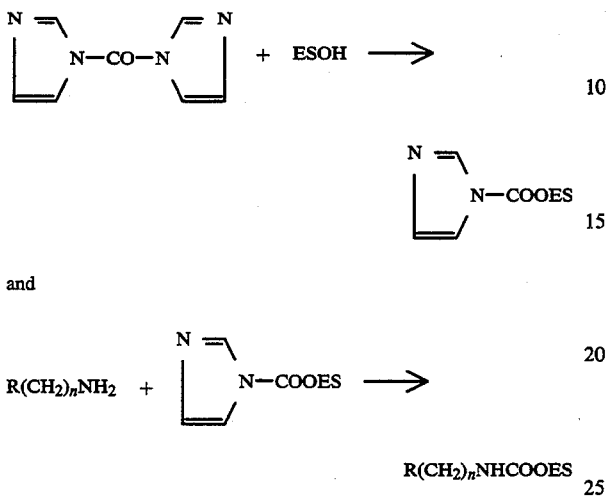

and

R(CH₂)ₙNH₂ +

R(CH₂)ₙNHCOOES

Compound (I), where R1=H, is thus obtained. For the preparation of compound (I), where R1=alkyl group, before proceeding to step c), the amino derivative (IV) is alkylated to form the corresponding secondary amino derivative.

Compounds as per general formula (I) and their pharmacologically acceptable salts exhibit a higher cholinesterase activity depression and reduced side effects if compared with the compounds mentioned in the prior art. Therefore, the present invention also contemplates the use of compounds as per general formula (I) and of their pharmacologically acceptable salts in the preparation of pharmaceutical compositions suitable for therapeutic use because of their inhibiting acetylcholinesterase action.

DETAILED DESCRIPTION OF THE INVENTION

The characteristics of and the advantages offered by the aminoalkylcarbamic esters of eseroline suitable for use as cholinesterase activity inhibitors and the relative preparation process according to the present invention are going to be illustrated in more detail.

In the present patent the term eseroline indicates (3aS,8aR)-1,2,3,3a,8,8a-hexahydro-1,3a,8-trimethylpyrrol[2,3-b]indol-5-ol. Said compounds have the following general formula (I)

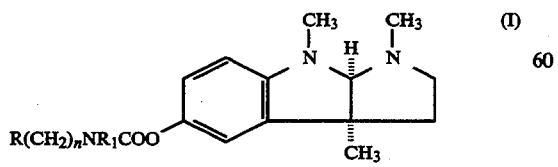

where n is an integer from 2 to 20; R1 may be H, methyl, ethyl, propyl, and isopropyl; and R is an amine selected out of the group consisting of

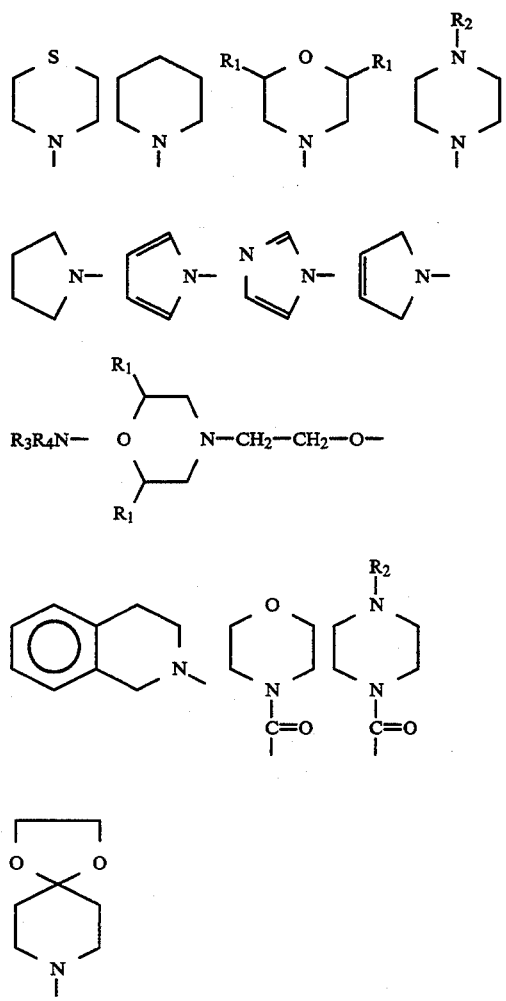

where R2 is linear or branched $C_1$-$C_4$ alkyl, or acyl or benzyl; R3 and R4 are linear or branched $C_1$-$C_4$ alkyls, or benzyl or methoxyethyl, methoxypropyl, methoxybutyl.

Compounds as per general formula (I) are prepared according to the following process:

a) heterocyclic compound RH, where R is as defined above, is caused to react with Ω-haloalkylphthalimide as per formula (III)

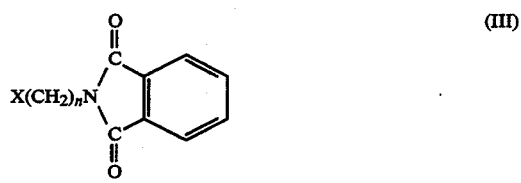

(III)

where X is selected out of the group consisting of F, Cl, Br, and I. The reaction is carried out in the presence of a solvent selected among ethyl ether, acetonitrile and tetrahydrofuran, at room temperature, and with a molar Patio of RH to (III) ranging from 3:1 to 1:1. The following compound is obtained:

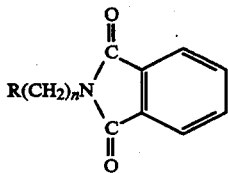

b) the compound obtained under a) is treated with hydrazine aqueous solution in order to remove the phthalic group.

The reaction is carried out in methanol and the mixture is heated to reflux. Solvents are removed by evaporation under reduced pressure and the product is purified by chromatography.

A primary amino derivative as per formula (IV)

$$R(CH_2)_nNH_2 \qquad (IV)$$

is obtained;

c) carbonyl diimidazole is caused to react with eseroline (ESOH) according to the following raction:

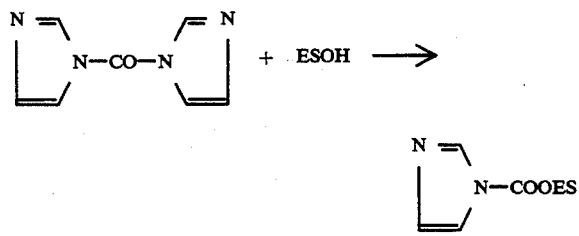

The reaction is carried out in the presence of a solvent selected among methylene chloride, toluene, benzene, xylene, DMF at room temperature, and with a molar ratio of carbonyl diimidazole to eseroline ranging from 3:1 to 1:1.

The reaction mixture is added with compound (IV) to promote the following reaction

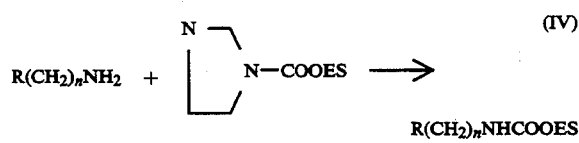

The reaction is carried out at room temperature with an initial molar ratio of (IV) to carbonyl diimidazole ranging from 2:1 to 1:1. The solvent is removed by evaporation under reduced pressure and the product is purified by chromatography.

Compounds (I) with R1=H are obtained with the process described hereinabove. For the preparation of compounds (I), where R1=methyl, ethyl, propyl or isopropyl, compound (IV), before being used in step c), is alkylated to form the corresponding secondary amino derivative. This can be obtained by treatment of compound (IV) with dimethylphosphate or with ethyl or propyl or isopropyl halides or by monobenzylation with benzyl bromide followed by treatment with alkyl halide and subsequent debenzylation by hydrogenolysis.

Compounds as per formula (I) can be salified with pharmacologically acceptable acids selected out of the group consisting of HCl, HBr, $H_2SO_4$, $H_3PO_4$, $HClO_4$, citric acid, tartaric acid, maleic acid, salicylic acid, fumaric acid, succinic acid, and oxalic acid. Salification is obtained by dissolving the compound as per formula (I) in an organic solvent, such as ethyl ether, methanol, ethanol, isopropanol, n-butanol, diisopropyl ether, and causing the obtained solution to react with the selected acid dissolved in one of the aforesaid solvents.

For salification, the preferred solvent-reagents ratios range from 5 to 25 ml solvent/g compound (I) and from 5 to 35 ml solvent/g acid. The salt obtained is purified by the usual techniques: solvent extraction, chromatography and organic compounds crystallization.

The following examples, which are concerned with the preparation of the claimed compounds, are conveyed by way of indication, not of limitation.

EXAMPLE 1

PREPARATION OF MORPHOLINYLETHYLCARBAMOYLESEROLINE a) Preparation of 2-morpholinylethylphthalimide 2-Bromoethylphthalimide (508 mg; 2.0 mmoles) and morpholine (0.35 ml; 4.0 mmoles) were dissolved in anhydrous ethyl ether (5 ml). The mixture was allowed to stir at room temperature for 30 hours approx. The reaction was discontinued by solvent evaporation under reduced pressure. The obtained residue was purified by chromatography on silica gel ($CH_2Cl_2$/MeOH 95:5) yielding 271 mg of pure product.

Yield 52%. Analysis: calcd. C 64.60; H 6.20; N 10.76 found C 64.51; H 6.25; N 10.98 b) Preparation of 2-morpholinylethylamine

Hydrazine (aqueous solution at 35% by wt.) (0.15 ml; 1.6 mmoles) was added to 2-morpholinylethylphthalimide (208 mg; 0.8 mmoles) in methanol (5 ml) and the resulting solution was refluxed. After one hour, the solvents were evaporated under reduced pressure; the obtained product was taken up with $CHCl_3$ and the collected precipitate was filtered. $CHCl_3$ was evaporated under reduced pressure yielding a solid (115 mg). The product was purified by silica gel chromatography with gradient, eluting with $CHCl_3$/MeOH/$H_2O$, 65:35:5, to remove the products migrating almost at the eluent front, followed by eluting with $CHCl_3$/MeOH/$NH_4OH$, 65:35:2, to isolate the desired product of very intense colour by ninhydrin and iodine reactions.

65 mg of pure product were obtained. Yield 62%. Analysis: calcd. C 55.36; H 10.84; N 21.51 found C 55.51; H 10.55; N 21.98.

c) Preparation of N-morpholinylethylcarbamoyleseroline

Carbonyl diimidazole (36 mg; 0.22 mmoles) was added to a degassed solution of eseroline (25 mg; 0.11 mmoles) in anhydrous $CH_2Cl_2$ (5 ml). The solution was allowed to stir at room temperature for 1 hour approx., then added with 2-morpholinylethylamine (43 mg; 0.33 mmoles) in anhydrous $CH_2Cl_2$ (10 ml). Stirring at room temperature was continued for additional 2 hours approx. after the addition of 2-morpholinylethylamine. The reaction course was controlled by TLC ($CHCl_3$/MeOH 87:13). At the end of the reaction, the solvent was evaporated under reduced pressure yielding an oil (50 mg), which was purified by column chromatography on silica gel eluting with acetone/MeOH 8:2.

8 mg of pure product were obtained. Yield 20%. $^1$H-NMR (200 MHz, $CDCl_3$): δ6.60 (m, 2H); 6.35 (d, 1H); 5.45 (s broad, 1H); 4.16 (s, 1H); 3.70 (m, 4H); 3.37

(m, 2H); 2.93 (s, 3H); 2.55 (s, 3H); 2.60–2.45 (m, 8H); 1.98 (m, 2H); 1.43 (s, 3H). Analysis: calcd. C 64.15; H 8.08; N 14.95 found C 64.52; H 8.25; N 14.98

EXAMPLE 2

PREPARATION OF MORPHOLINYLPROPYLCARBAMOYLESEROLINE a) Preparation of 3-morpholinylpropylphthalimide 3-Bromopropylphthalimide (536 mg; 2.0 mmoles) and morpholine (0.35 ml; 4.0 mmoles) were dissolved in anhydrous ethyl ether (5 ml). Reaction times and process as per Example 1.

291 mg of pure product were thus obtained. Yield 53%. Analysis: calcd. C 65.68; H 6.61; N 10.21 found C 65.61; H 6.75; N 10.18 b) Preparation of 3-morpholinylpropylamine

Hydrazine (aqueous solution at 35% by wt.) (0.15 ml; 1.6 mmoles) was added to 3-morpholinylpropylphthalimide (219 mg; 0.8 mmoles) in methanol (5 ml) and the resulting solution was refluxed. Reaction times and process as per Example 1.

75 mg of pure product were obtained, Yield 65%. Analysis: calcd. C 58.30; H 11.18; N 19.42 found C 58.00; H 11.25; N 19.88.

c) Preparation of N-morpholinylpropylcarbamoyleseroline

Carbonyl diimidazole (36 mg; 0.22 mmoles) was added to a degassed solution of eseroline (25 mg; 0.11 mmoles) in anhydrous $CH_2Cl_2$ (5 ml). The solution was allowed to stir at room temperature for 1 hour approx., then 3-morpholinylpropylamine (48 mg; 0.33 mmoles) in anhydrous $CH_2Cl_2$ (10 ml) was added. Stirring at room temperature was continued for additional 2 hours approx. after the addition of 3-morpholinylpropylamine. Reaction process as per Example 1.

16 mg of product were obtained. Yield 38%. $^1$H-NMR (200 MHz, $CDCl_3$): δ6.85 (m, 2H); 6.50 (d, 1H); 6.27 (s broad, 1H); 4.70 (s, 1H); 3.78 (t, 4H); 3.38 (m, 2H); 3.02 (s, 3H); 2.65 (s, 3H); 2.70–2.30 (m, 8H); 2.15 (m, 2H); 1.77 (m, 2H); 1.55 (s, 3H). Analysis: calcd. C 64.93; H 8.30; N 14.41 found C 64.81; H 8.15; N 14.70

EXAMPLE 3

PREPARATION OF MORPHOLINYLBUTYLCARBAMOYLESEROLINE a) Preparation of 4-morpholinylbutylphthalimide 4-Bromobutylphthalimide (564 mg; 2.0 mmoles) and morpholine (0.35 ml; 4.0 mmoles) were dissolved in anhydrous ethyl ether (5 ml). Reaction times and process as per Example 1.

317 mg of pure product were obtained. Yield 55%. Analysis: calcd. C 66.65; H 6.99; N 9.71 found C 66.41; H 6.77; N 9.99 b) Preparation of 4-morpholinylbutylamine

Hydrazine (aqueous solution at 35% by wt.) (0.15 ml; 1.6 mmoles) was added to 4-morpholinylbutylphthalimide (231 mg; 0.8 mmoles) in methanol (5 ml) and the resulting solution was refluxed. Reaction times and process as per Example 1.

86 mg of pure product were obtained. Yield 68%. Analysis: calcd. C 60.73; H 11.47; N 17.70 found C 60.53; H 11.27; N 17.45.

c) Preparation of N-morpholinylbutylcarbamoyleseroline

Carbamoyl diimidazole (36 mg; 0.22 mmoles) was added to a degassed solution of eseroline (25 mg; 0.11 mmoles) in anhydrous $CH_2Cl_2$ (5 ml). The solution was allowed to stir at room temperature for 1 hour approx., then 4-morpholinylbutylamine (52 mg; 0.33 mmoles) in anhydrous $CH_2Cl_2$ (10 ml) was added. Stirring at room temperature was continued for additional 2 hours approx. after the addition of 4-morpholinylbutylamine. Reaction times and process as per Example 1.

14 mg of pure product were obtained. Yield 32%. $^1$H-NMR (200 MHz, $CDCl_3$): δ6.80 (m, 2H); 6.34 (d, 1H); 5.92 (s broad, 1H); 4.15 (s, 1H); 3.73 (t, 4H); 3.25 (m, 2H); 2.88 (s, 3H); 2.55 (s, 3H); 2.80-2.33 (m, 8H); 1.95 (m, 2H) 1.75 (m, 2H); 1.58 (m, 2H); 1.45 (s, 3H). Analysis: calcd. C 65.65; H 8.51; N 13.91 found C 65.55; H 8.33; N 14.00

EXAMPLE 4

PREPARATION OF MORPHOLINYLPENTYLCARBAMOYLESEROLINE a) Preparation of 5-bromopentylphthalimide Potassium phthalimide (5.4 mmoles) was added to a solution of 1,5-dibromopentane (3.72 g; 16.2 mmoles) in dimethylformamide (8 ml) and heated to 80° C. approx. under stirring. After 2 hours, water was added and the solution was repeatedly extracted with ether. The collected organic phases were washed with water, dried on $Na_2SO_4$ and evaporated under reduced pressure to give a solid (4.50 g), which was purified by chromatography on silica gel (Etp/$Et_2O$ 8:2) yielding 2.38 g of a white solid. Yield 68%.

Analysis: calcd. C 72.20; H 6.53; N 6.47 found C 72.01; H 6.55; N 6.32.

b) Preparation of 5-morpholinylpentylphthalimide

5-Bromopentylphthalimide (432 mg; 2.0 mmoles) and morpholine (0.35 ml; 4.0 mmoles) were dissolved in anhydrous ethyl ether (5 ml). Reaction times and process as per Example 1.

326 mg of pure product were obtained. Yield 54%. Analysis: calcd. C 67.53; H 7.33; N 9.26 found C 67.51; H 7.25; N 9.28 c) Preparation of 5-morpholinylpentylamine

Hydrazine (aqueous solution at 35% by wt.) (0.15 ml; 1.6 mmoles) was added to 5-morpholinylpentylphthalimide (242 mg; 0.8 mmoles) in methanol (5 ml) and the resulting solution was refluxed. Reaction times and process as per Example 1.

81 mg of pure product were obtained. Yield 59% Analysis: calcd. C 62.75; H 11.70; N 16.25 found C 62.87; H 11.83; N 16.38.

d) Preparation of N-morpholinylpentylcarbamoyleseroline

Carbamoyl diimidazole (36 mg; 0.22 mmoles) was added to a degassed solution of eseroline (25 mg; 0.11 mmoles) in anhydrous $CH_2Cl_2$ (5 ml). The solution was allowed to stir at room temperature for 1 hour approx., then 8-morpholinyloctylamine (57 mg; 0.33 mmoles) in anhydrous $CH_2Cl_2$ (10 ml) was added. Stirring at room temperature was continued for additional 2 hours approx. after the addition of 8-morpholinyloctylamine. Reaction times and process as per Example 1.

27 mg of pure product were obtained. Yield 60%. Analysis: calcd. C 66.32; H 8.71; N 13.44 found C 66.31; H 8.88; N 13.44.

EXAMPLE 5

PREPARATION OF MORPHOLINYLHEXYLCARBAMOYLESEROLINE a) Preparation of 6-bromohexylphthalimide Potassium phthalimide (5.4 mmoles) was added to a solution of 1,6-dibromohexane (3.95 g; 16.2 mmoles) in dimethylformamide (8 ml) and heated to 80° C. approx. under stirring. Reaction times and process as per Example 4.

2.46 g of pure product were obtained. Yield 66%. Analysis: calcd. C 73.02; H 7.00; N 6.08 found C 72.83; H 7.25; N 5.98.

b) Preparation of 6-morpholinylhexylphthalimide

6-Bromohexylphthalimide (633 mg; 2.0 mmoles) and morpholine (0.35 mg; 4.0 mmoles) were dissolved in anhydrous ethyl ether (5 ml). Reaction times and process as per Example 1.

342 mg of pure product were obtained. Yield 54%. Analysis: calcd. C 68.33; H 7.65; N 8.85 found C 68.22; H 7.75; N 8.99 c) Preparation of 6-morpholinylhexylamine

Hydrazine (aqueous solution at 35% by wt.) (0.15 ml; 1.6 mmoles) was added to 6-morpholinylhexylphthalimide (253 mg; 0.8 mmoles) in methanol (5 ml) and the resulting solution was refluxed. Reaction times and process as per Example 1.

94 mg of pure product were obtained. Yield 63%. Analysis: calcd. C 64.48; H 11.90; N 15.03 found C 64.52; H 12.01; N 14.97.

d) Preparation of N-morpholinylhexylcarbamoyleseroline

Carbamoyl diimidazole (36 mg; 0.22 mmoles) was added to a degassed solution of eseroline (25 mg; 0.11 mmoles) in anhydrous $CH_2Cl_2$ (5 ml). The solution was allowed to stir at room temperature for 1 hour approx., then 6-morpholinylhexylamine (61 mg; 0.33 mmoles) in anhydrous $CH_2Cl_2$ (10 ml) was added. Stirring at room temperature was continued for additional 2 hours approx. after the addition of 6- morpholinylhexylamine. Reaction times and process as per Example 1.

24 mg of pure product were obtained. Yield 51%. Analysis: calcd. C 66.95; H 8.90; N 13.01 found C 67.02; H 8.99; N 13.21.

EXAMPLE 6

PREPARATION OF MORPHOLINYLHEPTYLCARBAMOYLESEROLINE a) Preparation of 7-bromoheptylphthalimide Potassium phthalimide (5.4 mmoles) was added to a solution of 1,7-dibromoheptane (4.18 g; 16.2 mmoles) in dimethylformamide (8 ml) and heated to 80° C. approx. under stirring. Reaction times and process as per Example 4.

2.73 g of pure product were obtained. Yield 69%. Analysis: calcd. C 73.74; H 7.43; N 5.73 found C 73.70; H 7.24; N 5.77.

b) Preparation of 7-morpholinylheptylphthalimide

7-Bromoheptylphthalimide (489 mg; 2.0 mmoles) and morpholine (0.35 ml; 4.0 mmoles) were dissolved in anhydrous acetonitrile (5 ml). Reaction times and process as per Example 1.

324 mg of pure product were obtained. Yield 49%. Analysis: calcd. C 69.01; H 7.93; N 8.47 found C 68.91; H 8.06; N 8.57 c) Preparation of 7-morpholinylheptylamine

Hydrazine (aqueous solution at 35% by wt.) (0.15 ml; 1.6 mmoles) was added to 7-morpholinylheptylphthalimide (264 mg; 0.8 mmoles) in methanol (5 ml) and the resulting solution was refluxed. Reaction times and process as per Example 1.

99 mg of pure product were obtained. Yield 62%. Analysis: calcd. C 65.96; H 12.08; N 13.98 found C 66.13; H 11.89; N 13.98.

d) Preparation of N-morpholinylheptylcarbamoyleseroline

Carbonyl diimidazole (36 mg; 0.22 mmoles) was added to a solution of eseroline (25 mg; 0.11 mmoles) in anhydrous toluene (5 ml). The solution was allowed to stir at room temperature for 1 hour approx., then 8-morpholinyloctylamine (66 mg: 0.33 mmoles) in anhydrous toluene (10 ml) was added. Stirring at room temperature was continued for additional 2 hours approx. after the addition of 8-morpholinyloctylamine. Reaction times and process as per Example 1.

24 mg of pure product were obtained. Yield 51%. Analysis: calcd. C 67.54; H 9.07; N 12.60 found C 67.51; H 9.15; N 12.97.

EXAMPLE 7

PREPARATION OF MORPHOLINYLOCTYLCARBAMOYLESEROLINE a) Preparation of 8-bromooctylphthalimide Potassium phthalimide (5.4 mmoles) was added to a solution of 1,8-dibromooctane (4.41 g; 16.2 mmoles) in dimethylformamide (8 ml) and heated to 80° C. approx. under stirring. Reaction times and process as per Example 4.

2.8 g of pure product were obtained. Yield 67%. Analysis: calcd. C 74.39; H 7.80; N 5.42 found C 74.54; H 7.78; N 5.08.

b) Preparation of 8-morpholinyloctylphthalimide

8-Bromooctylphthalimide (676 mg; 2.0 mmoles) and morpholine (0.35 ml; 4.0 mmoles) were dissolved in anhydrous acetonitrile (5 ml). Reaction times and process as per Example 1.

331 mg of pure product were obtained. Yield 48%. Analysis: calcd. C 69.74; H 8.19; N 8.13 found C 70.05; H 8.25; N 8.00 c) Preparation of 8-morpholinyloctylamine

Hydrazine (aqueous solution at 35% by wt.) (0.15 ml; 1.6 mmoles) was added to 8-morpholinyloctylphthalimide (275 mg; 0.8 mmoles) in methanol (5 ml) and the resulting solution was refluxed. Reaction times and process as per Example 1.

102 mg of pure product were obtained. Yield 60%. Analysis: calcd. C 67.27; H 12.23; N 13.06 found C 67.02; H 12.25; N 13.08.

d) Preparation of N-morpholinyloctylcarbamoyleseroline

Carbonyl diimidazole (36 mg: 0.22 mmoles) was added to a degassed solution of eseroline (25 mg; 0.11 mmoles) in anhydrous toluene (5 ml). The solution was allowed to stir at room temperature for 1 hour approx., then 8-morpholinyloctylamine (70 mg; 0.33 mmoles) in anhydrous toluene (10 ml) was added. Stirring at room temperature was continued for additional 2 hours approx. after the addition of 8-morpholinyloctylamine. Reaction times and process as per Example 1.

36 mg of pure product were obtained. Yield 72%. $^1$H-NMR (200 MHz, $CDCl_3$): δ6.78 (m, 2H); 6.32 (d, 1H); 4.92 (s broad, 1H); 4.18 (s, 1H); 3.72 (m, 4H); 3.20 (m, 2H); 2.91 (s, 3H); 2.55 (s, 3H); 2.48–2.23 (m, 8H); 1.92 (m, 4H); 1.45 (s, 3H); 1.31 (m, 12H). Analysis: calcd. C 68.09; H 9.23; N 12.21 found C 68.00; H 9.00; N 12.22.

EXAMPLE 8

PREPARATION OF MORPHOLINYLDODECYLCARBAMOYLESEROLINE a) Preparation of 12-bromododecylphthalimide Potassium phthalimide (1 g; 5.4 mmoles) was added to a solution of 1,8-dibromododecane (5.31 g; 16.2 mmoles) in dimethylformamide (8 ml) and heated to 80° C. approx. under stirring. Reaction times and process as per Example 4.

3.46 g of pure product were obtained. Yield 68%. Analysis: calcd. C 76.40; H 8.98; N 4.45 found C 76.51; H 9.12; N 4.06.

b) Preparation of 12-morpholinyldodecylphthalimide

12-Bromododecytphthalimide (623 mg; 2.0 mmoles) and morpholine (0.35 ml; 4.0 mmoles) were dissolved in anhydrous ethyl ether (5 ml). Reaction times and process as per Example 1.

392 mg of pure product were obtained. Yield 49%. Analysis: calcd. C 71.97; H 9.06; N 6.99 found C 72.07; H 8.94; N 7.17.

c) Preparation of 12-morpholinyldodecylamine

Hydrazine (aqueous solution at 35% by wt.) (0.15 ml; 1.6 mmoles) was added to 12-morpholinyldodecylphthalimide (320 mg; 0.8 mmoles) in methanol (5 ml) and the resulting solution was refluxed. Reaction times and process as per Example 1.

147 mg of pure product were obtained. Yield 68%. Analysis: calcd. C 71.06; H 12.67; N 10.35 found C 70.89; H 12.33; N 10.43.

d) Preparation of N-morpholinyldodecylcarbamoyleseroline

Was added to a degassed solution of eseroline (25 mg; 0.11 mmoles) in anhydrous CH$_2$Cl$_2$ (5 ml). The solution was allowed to stir at room temperature for 1 hour approx., then 12-morpholinyldodecylamine (89 mg; 0.33 mmoles) in anhydrous CH$_2$Cl2 (10 ml) was added. Stirring at room temperature was continued for additional 2 hours approx. after the addition of 12-morpholinyldodecylamine. Reaction times and process as per Example 1.

27 mg of pure product were obtained. Yield 48%. Analysis: calcd. C 70.00; H 9.79; N 10.88 found C 70.01; H 9.99; N 10.98.

EXAMPLE 9

PREPARATION OF N-METHYLPIPERAZINYLETHYLCARBAMOYLESEROLINE a) Preparation of 2-(N-methylpiperazinyl) ethylphthalimide 2-Bromoethylphthalimide (508 mg; 2.0 mmoles) and N-methylpiperazine (0.44 ml; 4.0 mmoles) were dissolved in anhydrous ethyl ether (5 ml). Reaction times and process as per Example 1.

272 mg of pure product were obtained. Yield 50%. Analysis: calcd. C 66.16; H 6.66; N 15.42 found C 65.97; H 6.65; N 15.55.

b) Preparation of 2-(N-methylpiperazinyl)ethylamine

Hydrazine (aqueous solution at 35% by wt.) (0.15 ml; 1.6 mmoles) was added to 2-(N-methylpiperazinyl)ethylphthalimide (218 mg; 0.8 mmoles) in methanol (5 ml) and the resulting solution was refluxed. Reaction times and process as per Example 1.

73 mg of pure product were obtained. Yield 64%. Analysis: calcd. C 58.71; H 11.97; N 29.33 found C 58.91; H 12.00; N 29.35.

c) Preparation of N-(N-methylpiperazinylethyl)carbamoyleseroline

Carbonyl diimidazole (36 mg; 0.22 mmoles) was added to a solution of eseroline (25 mg; 0.11 mmoles) in anhydrous benzene (5 ml). The solution was allowed to stir at room temperature for 1 hour approx., then 2-(N-methylpiperazinyl)ethylamine (47 mg; 0.33 mmoles) in anhydrous benzene (10 ml) was added. Stirring at room temperature was continued for additional 2 hours approx. after the addition of 2-(N-methylpiperazinyl)ethylamine. Reaction times and process as per Example 1.

18 mg of pure product were obtained. Yield 45%. Analysis: calcd. C 65.09; H 8.58; N 18.06 found C 65.12; H 8.73; N 18.22.

EXAMPLE 10

PREPARATION OF N-METHYLPIPERAZINYLPROPYLCARBAMOYLESEROLINE a) Preparation of 3-(N-methylpiperazinyl)propylphthalimide 3-Bromopropylphthalimide (536 mg; 2.0 mmoles) and N-methylpiperazine (0.44 ml; 4.0 mmoles) were dissolved in anhydrous ethyl ether (5 ml). Reaction times and process as per Example 1.

292 mg of pure product were obtained. Yield 51%. Analysis: calcd. C 67.12; H 7.04; N 14.67 found C 66.99; H 7.00; N 14.87.

b) Preparation of 3-(N-methylpiperazinyl)propylamine

Hydrazine (aqueous solution at 35% by wt.) (0.15 ml; 1.6 mmoles) was added to 3-(N-methylpiperazinyl)propylphthalimide (229 mg; 0.8 mmoles) in methanol (5 ml) and the resulting solution was refluxed. Reaction times and process as per Example 1.

80 mg of pure product were obtained. Yield 64%. Analysis: calcd. C 61.11; H 12.18; N 26.71 found C 61.01; H 12.35; N 27.02.

c) Preparation of N-(N-methylpiperazinylpropyl)carbamoyleseroline

Carbonyl diimidazole (36 mg; 0.22 mmoles) was added to a solution of eseroline (25 mg; 0.11 mmoles) in anhydrous benzene (5 ml). The solution was allowed to stir at room temperature for 1 hour approx., then 3-(N-methylpiperazinyl)propylamine (52 mg; 0.33 mmoles) in anhydrous benzene (10 ml) was added. Stirring at room temperature was continued for additional 2 hours approx. after the addition of 3-(N-methylpiperazinyl)propylamine. Reaction times and process as per Example 1.

8 mg of pure product were obtained. Yield 19%. Analysis: calcd. C 65.81; H 8.79; N 17.43 found C 65.51; H 9.05; N 17.77.

EXAMPLE 11

PREPARATION OF N-METHYLPIPERAZINYLBUTYLCARBAMOYLESEROLINE a) Preparation of 4-(N-methylpiperazinyl)butylphthalimide 4-Bromoethylphthalimide (564 mg; 2.0 mmoles) and N-methylpiperazine (0.44 ml; 4.0 mmoles) were dissolved in anhydrous ethyl ether (5 ml). Reaction times and process as per Example 1.

288 mg of pure product were obtained. Yield 48%. Analysis: calcd. C 67.98; H 7.38; N 13.98 found C 68.14; H 7.57; N 14.07.

b) Preparation of 4-(N-methylpiperazinyl)butylamine

Hydrazine (aqueous solution at 35% by wt.) (0.15 ml; 1.6 mmoles) was added to 4-(N-methylpiperazinyl)butylphthalimide (240 mg; 0.8 mmoles) in methanol (5 ml) and the resulting solution was refluxed. Reaction times and process as per Example 1.

90 mg of pure product were obtained. Yield 66%. Analysis: calcd. C 63.12; H 12.36; N 24.52 found C 63.31; H 12.56; N 24.44.

c) Preparation of N-(N-methylpiperazinylbutyl)carbamoyleseroline

Carbonyl diimidazole (36 mg; 0.22 mmoles) was added to a solution of eseroline (25 mg; 0.11 mmoles) in anhydrous benzene (5 ml). The solution was allowed to stir at room temperature for 1 hour approx., then 4-(N-methylpiperazinyl)butylamine (56 mg; 0.33 mmoles) in anhydrous benzene (10 ml) was added. Stirring at room temperature was continued for additional 2 hours approx. after the addition of 4-(N-methylpiperazinyl)butylamine. Reaction times and process as per Example 1.

20 mg of pure product were obtained. Yield 44%. Analysis: calcd. C 66.48; H 8.98; N 16.85 found C 66.33; H 9.02; N 17.00.

EXAMPLE 12

PREPARATION OF N-METHYLPIPERAZINYLHEXYLCARBAMOYLESEROLINE a) Preparation of 6-(N-methylpiperazinyl)hexylphthalimide 6-Bromohexylphthalimide (460 mg; 2.0 mmoles) and N-methylpiperazine (0.44 ml; 4.0 mmoles) were dissolved in anhydrous ethyl ether (5 ml). Reaction times and process as per Example 1.

302 mg of pure product were obtained. Yield 46%. Analysis: calcd. C 69.49; H 7.98; N 12.98 found C 69.25; H 8.13; N 13.08.

b) Preparation of 6-(N-methylpiperazinyl)hexylamine

Hydrazine (aqueous solution at 35% by wt.) (0.15 ml; 1.6 mmoles) was added to 6-(N-methylpiperazinyl)hexylphthalimide (263 mg; 0.8 mmoles) in methanol (5 ml) and the resulting solution was refluxed. Reaction times and process as per Example 1.

112 mg of pure product were obtained. Yield 70%. Analysis: calcd. C 66.29; H 12.64; N 21.07 found C 66.07; H 12.77; N 20.99.

c) Preparation of N-(N-methylpiperazinythexyl)carbamoyleseroline

Carbonyl diimidazole (36 mg; 0.22 mmoles) was added to a solution of eseroline (25 mg; 0.11 mmoles) in anhydrous benzene (5 ml). The solution was allowed to stir at room temperature for 1 hour approx., then 6-(N-methylpiperazinyl)hexylamine (66 mg; 0.33 mmoles) in anhydrous benzene (10 ml) was added. Stirring at room temperature was continued for additional 2 hours approx. after the addition of 6-(N-methylpiperazinyl)hexylamine. Reaction times and process as per Example 1.

30 mg of pure product were obtained. Yield 60%. Analysis: calcd. C 67.69; H 9.32; N 15.78 found C 68.00; H 9.33; N 15.97.

EXAMPLE 13

PREPARATION OF N-METHYLPIPERAZINYLOCTYLCARBAMOYLESEROLINE a) Preparation of 8-(N-methylpiperazinyl)octylphthalimide 8-Bromooctylphthalimide (516 mg; 2.0 mmoles) and N-methylpiperazine (0.44 ml; 4.0 mmoles) were dissolved in anhydrous ethyl ether (5 ml). Reaction times and process as per Example 1.

356 mg of pure product were obtained. Yield 50%. Analysis: calcd. C 70.76; H 8.48; N 11.78 found C 70.80; H 8.53; N 11.83.

b) Preparation of 8-(N-methylpiperazinyl)octylamine

Hydrazine (aqueous solution at 35% by wt.) (0.15 ml; 1.6 mmoles) was added to 8-(N-methylpiperazinyl)octylphthalimide (285 mg; 0.8 mmoles) in methanol (5 ml) and the resulting solution was refluxed. Reaction times and process as per Example 1.

118 mg of pure product were obtained. Yield 65%. Analysis: calcd. C 68.67; H 12.86; N 18.47 found C 68.50; H 12.66; N 18.54.

c) Preparation of N-(N-methylpiperazinyloctyl)carbamoyleseroline

Carbonyl diimidazole (36 mg; 0.22 mmoles) was added to a solution of eseroline (25 mg; 0.11 mmoles) in anhydrous benzene (5 ml). The solution was allowed to stir at room temperature for 1 hour approx., then 8-(N-methylpiperazinyl)octylamine (75 mg; 0.33 mmoles) in anhydrous benzene (10 ml) was added. Stirring at room temperature was continued for additional 2 hours approx. after the addition of 8-(N-methylpiperazinyl)octylamine. Reaction times and process as per Example 1.

30 mg of pure product were obtained. Yield 57%. Analysis: calcd. C 68.76; H 9.62: N 14.84 found C 68.43; H 9.48; N 14.88.

EXAMPLE 14

PREPARATION OF PYRROLIDINYLOCTYLCARBAMOYLESEROLINE a) Preparation of 8-pyrrolidinyloctylphthalimide 8-Bromooctylphthalimide (517 mg; 2.0 mmoles) and pyrrolidine (0.33 ml; 4.0 mmoles) were dissolved in anhydrous ethyl ether (5 ml). Reaction times and process as per Example 1.

348 mg of pure product were obtained. Yield 53%. Analysis: calcd. C 73.14; H 8.59; N 8.53 found C 73.11; H 8.75; N 8.54.

b) Preparation of 8-pyrrolidinyloctylamine

Hydrazine (aqueous solution at 35% by wt.) (0.15 ml; 1.6 mmoles) was added to 8-pyrrolidinyloctylphthalimide (263 mg; 0.8 mmoles) in methanol (5 ml) and the resulting solution was refluxed. Reaction times and process as per Example 1.

105 mg of pure product were obtained. Yield 66%. Analysis: calcd. C 72.67; H 13.21; N 14.12 found C 72.72; H 13.25; N 14.07.

c) Preparation of N-pyrrolidinyloctylcarbamoyleseroline

Carbonyl diimidazole (36 mg; 0.22 mmoles) was added to a solution of eseroline (25 mg; 0.11 mmoles) in anhydrous CH$_2$Cl$_2$ (5 ml). The solution was allowed to stir at room temperature for 1 hour approx., then 8-pyrrolidinyloctylamine (65 mg; 0.33 mmoles) in anhydrous CH$_2$Cl$_2$ (10 ml) was added. Stirring at room temperature was continued for additional 2 hours approx. after the addition of 8-pyrrolidinyloctylamine. Reaction times and process as per Example 1.

24 mg of pure product were obtained. Yield 48%. Analysis: calcd. C 70.55; H 9.56; N 12.65 found C 70.51; H 9.55; N 12.74.

EXAMPLE 15

PREPARATION OF PIPERIDINYLOCTYLCARBAMOYLESEROLINE a) Preparation of 8-piperidinyloctylphthalimide 8-Bromooctylphthalimide (517 mg; 2.0 mmoles) and piperazine (0.40 ml; 4.0 mmoles) were dissolved in anhydrous ethyl ether (5 ml). Reaction times and process as per Example 1.

431 mg of pure product were obtained. Yield 63%. Analysis: calcd. C 73.65; H 8.83; N 8.18 found C 73.55; H 8.95; N 8.08.

b) Preparation of 8-piperidinyloctylamine

Hydrazine (aqueous solution at 35% by wt.) (0.15 ml; 1.6 mmoles) was added to 8-piperidinyloctylphthalimide (274 mg; 0.8 mmoles) in methanol (5 ml) and the resulting solution was refluxed. Reaction times and process as per Example 1.

119 mg of pure product were obtained. Yield 70%. Analysis: calcd. C 73.53; H 13.29; N 13.18 found C 73.51; H 13.25; N 13.08.

c) Preparation of N-piperidinyloctylcarbamoyleseroline

Carbonyl diimidazole (36 mg; 0.22 mmoles) was added to a solution of eseroline (25 mg; 0.11 mmoles) in anhydrous CH$_2$Cl$_2$ (5 ml). The solution was allowed to stir at room temperature for 1 hour approx., then 8-piperidinyloctylamine (70 mg; 0.33 mmoles) in anhydrous CH$_2$Cl$_2$ (10 ml) was added. Stirring at room temperature was continued for additional 2 hours approx. after the addition of 8-piperidinyloctylamine. Reaction times and process as per Example 1.

27 mg of pure product were obtained. Yield 54%. Analysis: calcd. C 71.02; H 9.71; N 12.26 found C 71.01; H 9.99; N 12.06.

EXAMPLE 16

PREPARATION OF N-(MORPHOLINYLOCTYL),N-METHYLCARBAMOYL ESEROLINE a) Preparation of N-(morpholinyloctyl),N-methylamine Dimethylsulphate (832 mg; 0.66 mmoles) was slowly added to 8-morpholinooctylamine (141 mg; 0.66 mmoles) under stirring, the temperature being kept below 70° C. throughout the addition. Stirring was continued overnight. Then the mixture was treated with sodium hydroxide solution (880 mg) in water (15 ml) and heated to boiling. After two hours, the mixture was cooled to room temperature. An oil was separated which was combined with the water layer benzene extracts: the mixture obtained was dried on Na$_2$SO$_4$ and evaporated under reduced pressure. The collected residue was; purified by silica gel chromatography, eluting with CHCl$_3$/MeOH/NH$_4$OH, 65:35:2, to separate the desired product of very intense colour by ninhydrin and iodine reactions.

75 mg of pure product were obtained. Yield 50%. Analysis: calcd. C 68.37; H 12.36; N 12.26 found C 68.33; H 12.35; N 12.28.

b) Preparation of N-(morpholinyloctyl),N-methyl carbamoyl eseroline Carbonyl diimidazole (36 mg; 0.22 mmoles) was added to a degassed solution of eseroline (25 mg; 0.11 mmoles) in anhydrous CH$_2$Cl$_2$ (5 ml). The solution was was allowed to stir at room temperature for 1 hour approx., then N-(morpholinyloctyl),N-methylamine (75 mg; 0.33 mmoles) in anhydrous CH$_2$Cl$_2$ (10 ml) was added. Stirring at room temperature was continued for additional 2 hours approx. after the addition of N-(morpholinyloctyl),N-methylamine. Reaction process as per Example 1.

36 mg of pure product were obtained. Yield 68%. Analysis: calcd. C 68.61; H 9.38; N 11.85 found C 68.52; H 9.28; N 11.87.

EXAMPLE 17

PREPARATION OF 8-(cis-2,6-DIMETHYL)MORPHOLINYLOCTYL-CARBAMOYLESEROLINE a) Preparation of 8-(cis/trans-2,6-dimethyl)morpholinyloctyl phthalimide 8-Bromooctylphthalimide (9 g; 26.60 mmoles) and 2,6-dimethyl morpholine (cis-trans isomers mix) (9.8 ml; 79.5 mmoles) were dissolved in anhydrous acetonitrile (50 ml). The mixture was allowed to stir at room temperature for 18 hours approx. The reaction was discontinued by solvent evaporation under reduced pressure. The collected residue was purified by chromatography on silica gel (CH$_2$Cl$_2$/MeOH 95:5). The first product isolated (Rf=0.7) is a light yellow oil (A trans) (2.04 g) , the second (Rf=0.4) is a yellow oil (B cis) (3.4 g). Total yield 54.8%.

Analysis: calcd. C 70.93; H 8.66; N 7.52 Compound A (trans isomer) found C 71.14; H 8.58; N 7.59 Compound B (cis isomer) found C 71.07; H 8.53; N 7.65 b) Preparation of 8-(cis-2,6-dimethyl)morpholinyloctylamine

Hydrazine (aqueous solution at 35% by wt.) (7 ml) was added to 8-(cis-2,6-dimethyl)morpholinyloctylphthalimide B (3.4 g; 9.12 mmoles) in methanol (25 ml) and the resulting solution was refluxed. After one hour, the solvents were evaporated under reduced pressure, the obtained product was taken up with CHCl$_3$ and the collected precipitate was filtered. CHCl$_3$ was evaporated under reduced pressure yielding a light yellow oil (1.614 g). Yield 73%. Analysis: calcd. C 69.37; H 12.47; N 11.46 found C 69.50; H 12.45; N 11.63.

c) Preparation of 8-(cis-2,6-dimethylmorpholinyl)octylcarbamoyl eseroline

Carbonyl diimidazole (719 mg; 4.44 mmoles) was added to a solution of eseroline (484 mg; 2.22 mmoles) in benzene (5 ml). The solution was allowed to stir at room temperature for 1 hour approx., then added with 8-(cis-2,6-dimethyl) morholinyloctylamine (1.614 mg; 6.66 mmoles) in anhydrous benzene (2 ml). Stirring at room temperature was continued for additonal 2 hours approx. after the addition of 8-(cis-2,6-dimethyl) morpholinyloctylamine. The reaction course was controlled by TLC (CHCl$_3$/MeOH 9:1). At the reaction end, the solvents were evaporated under reduced pressure yielding an oil (2.7 g), which was purified by column chromatography on silica gel eluting first with CHCl$_3$/MeOH, 9:1, and then with acetone/MeOH, 7:3.

An orange coloured oil were obtained (1.6 g). Yield 55.5%.

Analysis: calcd. C 69.10; H 9.53; N 11.51 found C 69.23; H 9.47; N 11.59

EXAMPLE 18

PREPARATION OF 8-(TRANS-2,6-DIMETHYL)MORPHOLINYLOC-TYLCARBAMOYL ESEROLINE a) Preparation of 8-(trans-2,6-dimethyl)morpholinyloctylamine Hydrazine (aqueous solution at 35% by wt.) (5 ml) was added to 8-(trans-2,6-dimethyl) morpholinyloctylphthalimide A (2.04 g; 5.47 mmoles), obtained as per Example 17a, in methanol (20 ml) and the resulting solution was refluxed. After 1 hour, the solvents were evaporated under reduced pressure and the obtained product was taken up with $CHCl_3$ under reduced pressure.

976 mg of a light yellow oil were obtained. Yield 73%. Analysis: calcd. C 69.37; H 12.47; N 11.56 found C 69.50; H 12.45; N 11.63.

b) Preparation of 8-(trans-2,6-dimethyl)morpholinyloctylcarbamoyl eseroline

A solution of eseroline (293 mg; 1.34 mmoles) in anhydrous benzene (5 ml) was added with carbonyl diimidazole (435 mg; 2.68 mmoles). The solution was allowed to stir at room temperature for 1 hour approx., then added with 8-(trans-2,6-dimethyl) morpholinyloctylamine (975 mg; 4.03 mmoles) in anhydrous benzene (2 ml). Stirring at room temperature was continued for additional 2 hours approx. after the addition of 8-(trans-2,6dimethyl)morpholinyloctylamine. The reaction course was controlled by TLC ($CHCl_3$/MeOH 9:1). At the reaction end, the solvents were evaporated under reduced pressure yielding an oil (1.7 g), which was purified by column chromatography on silica gel eluting with $CHCl_3$/MeOH, 9:1, and then with acetone/MeOH, 7:3. An orange coloured oil was obtained (268 mg). Yield 44%.

Analysis: calcd. C 69.10; H 9.53; N 11.54 found C 69.31; H 9.61; N 11.45

Other compounds obtained according to the present invention are shown in Table 1.

TABLE 1

Further examples of compounds obtained according to the invention

| Structural formula | Preparation | Number |
| --- | --- | --- |
| O-morpholine-N—(CH$_2$)$_9$—NH—C(=O)—N(H)-phenyl-eseroline | MF 233 | V |
| O-morpholine-N—(CH$_2$)$_{10}$—NH—C(=O)—O-phenyl-eseroline | MF 231 | VI |
| O-morpholine-N—(CH$_2$)$_{11}$—NH—C(=O)—O-phenyl-eseroline | MF 232 | VII |
| S-morpholine-N—(CH$_2$)$_8$—NH—C(=O)—O-phenyl-eseroline | MF 239 | VIII |
| dioxa-spiro-N—(CH$_2$)$_8$—NH—C(=O)—O-phenyl-eseroline | MF 265 | IX |

TABLE 1-continued

Further examples of compounds obtained according to the invention

| Structural formula | Preparation | Number |
|---|---|---|
| (structure) | MF 252 | X |
| (structure) | MF 275 | XI |
| (structure) | MF 245 | XII |
| (structure) | MF 262 | XIII |
| (structure) | MF 261 | XIV |
| (structure) | MF 273 | XV |
| (structure) | MF 270 | XVI |
| (structure) | MF 237 | XVII |

TABLE 1-continued

Further examples of compounds obtained according to the invention

| Structural formula | Preparation | Number |
|---|---|---|
| H₃C—CH₂\N—(CH₂)₁₀—NH—C(=O)—O—[aryl-physostigmine core] | MF 247 | XVIII |
| H₃C—CH₂\N—(CH₂)₁₂—NH—C(=O)—O—[aryl-physostigmine core] | MF 254 | XIX |
| Ph-CH₂—N(piperazine)N—(CH₂)₈—NH—C(=O)—O—[aryl-physostigmine core] | MF 266 | XX |
| CH₃—N(piperazine)N—(CH₂)₁₂—NH—C(=O)—O—[aryl-physostigmine core] | MF 229 | XXI |
| CH₃—N(piperazine)N—(CH₂)₁₀—NH—C(=O)—O—[aryl-physostigmine core] | MF 255 | XXII |
| CH₃—C(=O)—N(piperazine)N—(CH₂)₂—NH—C(=O)—O—[aryl-physostigmine core] | MF 246 | XXIII |
| CH₃—C(=O)—N(piperazine)N—(CH₂)₈—NH—C(=O)—O—[aryl-physostigmine core] | MF 240 | XXIV |
| morpholine-N—C(=O)—(CH₂)₇—NH—C(=O)—O—[aryl-physostigmine core] | MF 269 | XXV |

TABLE 1-continued

Further examples of compounds obtained according to the invention

| Structural formula | Preparation | Number |
|---|---|---|
| morpholine-N—CH₂—CH₂—O—(CH₂)₅—NH—C(=O)—O—[phenyl-physostigmine core] | MF 277 | XXVI |
| pyrrolidine-N—(CH₂)₁₀—NH—C(=O)—O—[phenyl-physostigmine core] | MF 253 | XXVII |
| (dipropyl)N—(CH₂)₈—NH—C(=O)—O—[phenyl-physostigmine core] | MF 256 | XXVIII |
| (dipropyl)N—(CH₂)₁₀—NH—C(=O)—O—[phenyl-physostigmine core] | MF 257 | XXIX |
| (dipropyl)N—(CH₂)₁₂—NH—C(=O)—O—[phenyl-physostigmine core] | MF 258 | XXX |
| (CH₃OCH₂CH₂)(CH₂OCH₂CH₂)N—(CH₂)₈—NH—C(=O)—O—[phenyl-physostigmine core] | MF 271 | XXXI |
| (phenyl)(CH₃)N—(CH₂)₈—NH—C(=O)—O—[phenyl-physostigmine core] | MF 263 | XXXII |
| piperidine-N—(CH₂)₁₀—NH—C(=O)—O—[phenyl-physostigmine core] | MF 248 | XXXIII |

TABLE 1-continued

Further examples of compounds obtained according to the invention

| Structural formula | Preparation | Number |
|---|---|---|
| [Structure: piperidine-N-(CH$_2$)$_{12}$-NH-C(=O)-O-phenyl-indoline with CH$_3$ groups] | MF 249 | XXXIV |
| [Structure: cyclopentenyl-N-(CH$_2$)$_8$-NH-C(=O)-O-phenyl-indoline with CH$_3$ groups] | MF 250 | XXXV |

Pharmacological tests

The compounds prepared as per the Examples reported above and several other compounds under the present invention (Table 1) were pharmacologically tested with a view to determining their inhibitory effect on acetylcholinesterase and butyrylcholinesterase activity. The used method had been developed by Ellman et al. (Ellman, G. L., Courtney, K. D., Andres, V., Featherstone, R. M.: "A New and Rapid Colorimetric Determination of Acetylcholinesterase Activity", Biochem. Pharm. 7, 88, 1961).

The tests were conducted on acetylcholinesterase from human erythrocyte and, respectively, from electric eel, and on butyrylcholinesterase from human serum, all produced by Sigma Chemical.

Table 2 shows the results obtained and, for purpose of comparison, the results obtained with the product of Example 30 of EPA 0253372, with physostigmine and heptastigmine.

TABLE 2

Cholinesterase Inhibition IC$_{50}$M

| Compound | t | AChE E.eel | t | AChE hRBC | t | AChE rat brain | t | BuChE hserum |
|---|---|---|---|---|---|---|---|---|
| MF 215 SF-92-057 | 10' | N.D. | 10' | $1.9 \times 10^{-5}$ | 10' | N.D. | 10' | $8.7 \times 10^{-4}$ |
| Ex 30 (EPA0253372) | | | 30' | $1.2 \times 10^{-5}$ | | | | |
| Hoechst-Roussel | | | 60' | $1.6 \times 10^{-5}$ | | | | |
| MF 214 | 10' | N.D. | 10' | $7.0 \times 10^{-7}$ | 10' | N.D. | 10' | $4.1 \times 10^{-6}$ |
| Ex. 1 | | | 30' | $1.4 \times 10^{-7}$ | | | | |
| | | | 60' | $1.1 \times 10^{-7}$ | | | | |
| MF 218 | 10' | N.D. | 10' | $3.8 \times 10^{-6}$ | 10' | N.D. | 10' | N.D. |
| Ex. 2 | | | | | | | | |
| MF 225 | 10' | $3.3 \times 10^{-4}$ | 10' | $7.6 \times 10^{-6}$ | 10' | $5.0 \times 10^{-4}$ | 10' | N.D. |
| Ex. 4 | | | 30' | $2.2 \times 10^{-6}$ | | | | |
| MF 227 | 10' | $1.2 \times 10^{-5}$ | 10' | $9.3 \times 10^{-7}$ | 10' | $8.2 \times 10^{-6}$ | 10' | $1.0 \times 10^{-7}$ |
| Ex. 5 | | | 30' | $3.8 \times 10^{-7}$ | | | | |
| MF 224 | 10' | $1.6 \times 10^{-6}$ | 10' | $3.8 \times 10^{-7}$ | 10' | $4.1 \times 10^{-6}$ | 10' | $3.0 \times 10^{-7}$ |
| Ex. 6 | | | 30' | $1.7 \times 10^{-7}$ | | | | |
| MF 217 | 10' | $3.3 \times 10^{-7}$ | 10' | $1.0 \times 10^{-7}$ | 10' | $8.8 \times 10^{-7}$ | 10' | $1.7 \times 10^{-7}$ |
| Ex. 7 | | | 30' | $7.6 \times 10^{-8}$ | | | | |
| | | | 60' | $6.3 \times 10^{-8}$ | | | | |
| MF 228 | 10' | $7.0 \times 10^{-8}$ | 10' | $7.0 \times 10^{-8}$ | 10' | $3.8 \times 10^{-7}$ | 10' | $1.0 \times 10^{-7}$ |
| Ex. 8 | | | 30' | $6.0 \times 10^{-8}$ | | | | |
| | | | 60' | $3.0 \times 10^{-8}$ | | | | |
| MF 230 | 10' | $2.0 \times 10^{-7}$ | 10' | $3.0 \times 10^{-8}$ | | | | |
| Ex. 13 | 30' | $8.0 \times 10^{-8}$ | 30' | $5.0 \times 10^{-8}$ | | | | |
| MF 201 | 10' | $5.5 \times 10^{-7}$ | 10' | $2.9 \times 10^{-7}$ | 10' | N.D. | 10' | $4.0 \times 10^{-8}$ |
| Heptastigmine | 30' | $4.1 \times 10^{-7}$ | | | | | | |
| | 60' | $4.4 \times 10^{-7}$ | | | | | | |
| ESERINE T. Fe-A-24A | 10' | $1.5 \times 10^{-7}$ | 10' | $4.7 \times 10^{-8}$ | 10' | N.D. | 10' | $7.2 \times 10^{-8}$ |
| Physostigmine | | | 30' | $2.9 \times 10^{-8}$ | | | | |
| | | | 60' | $0.4 \times 10^{-8}$ | | | | |
| MF 251 | 10' | N.D. | 10' | $0.7 \times 10^{-7}$ | 10' | N.D. | 10' | N.D. |
| Ex. 14 | | | | | | | | |
| MF 241 | 10' | N.D. | 10' | $1.0 \times 10^{-7}$ | 10' | N.D. | 10' | N.D. |
| Ex. 15 | | | | | | | | |
| MF 243 | 10' | N.D. | 10' | $7.4 \times 10^{-6}$ | 10' | N.D. | 10' | N.D. |
| Ex. 16 | | | | | | | | |
| MF 268 | 10' | N.D. | 10' | $0.7 \times 10^{-7}$ | 10' | N.D. | 10' | $1.8 \times 10^{-7}$ |
| Ex. 17 | | | | | | | | |
| MF 276 | 10' | N.D. | 10' | $0.7 \times 10^{-7}$ | 10' | N.D. | 10' | $2.5 \times 10^{-7}$ |
| Ex. 18 | | | | | | | | |
| MF 233 | 10' | $1.4 \times 10^{-7}$ | 10' | $0.6 \times 10^{-7}$ | 10' | N.D. | 10' | N.D. |
| V | | | | | | | | |
| MF 231 | 10' | $0.6 \times 10^{-7}$ | 10' | $0.4 \times 10^{-7}$ | 10' | N.D. | 10' | N.D. |

TABLE 2-continued

| | | Cholinesterase Inhibition IC$_{50}$M | | | | | | |
|---|---|---|---|---|---|---|---|---|
| Compound | t | AChE E.eel | t | AChE hRBC | t | AChE rat brain | t | BuChE hserum |
| VI | | | | | | | | |
| MF 232 | 10' | $0.7 \times 10^{-7}$ | 10' | $0.4 \times 10^{-7}$ | 10' | N.D. | 10' | N.D. |
| VII | | | | | | | | |
| MP 245 | 10' | N.D. | 10' | $5.5 \times 10^{-6}$ | 10' | N.D. | 10' | N.D. |
| XII | | | | | | | | |
| MF 229 | 10' | $0.4 \times 10^{-7}$ | 10' | $0.6 \times 10^{-7}$ | 10' | N.D. | 10' | N.D. |
| XXI | | | | | | | | |
| MF 255 | 10' | N.D. | 10' | $0.5 \times 10^{-7}$ | 10' | N.D. | 10' | N.D. |
| XXII | | | | | | | | |
| MF 246 | 10' | N.D. | 10' | $2.0 \times 10^{-5}$ | 10' | N.D. | 10' | N.D. |
| XXIII | | | | | | | | |
| MF 240 | 10' | N.D. | 10' | $2.4 \times 10^{-7}$ | 10' | N.D. | 10' | N.D. |
| XXIV | | | | | | | | |
| MF 252 | 10' | N.D. | 10' | $2.7 \times 10^{-8}$ | 10' | N.D. | 10' | N.D. |
| X | | | | | | | | |
| MF 275 | 10' | N.D. | 10' | $0.5 \times 10^{-7}$ | 10' | N.D. | 10' | N.D. |
| XI | | | | | | | | |
| MF 263 | 10' | N.D. | 10' | $0.5 \times 10^{-7}$ | 10' | N.D. | 10' | N.D. |
| XXXII | | | | | | | | |
| MF 266 | 10' | N.D. | 10' | $0.7 \times 10^{-7}$ | 10' | N.D. | 10' | N.D. |
| XX | | | | | | | | |
| MF 262 | 10' | N.D. | 10' | $0.3 \times 10^{-7}$ | 10' | N.D. | 10' | N.D. |
| XIII | | | | | | | | |
| MF 261 | 10' | N.D. | 10' | $0.2 \times 10^{-7}$ | | N.D. | 10' | N.D. |
| XIV | | | | | | | | |
| MF 269 | 10' | N.D. | 10' | $1.2 \times 10^{-7}$ | 10' | N.D. | 10' | N.D. |
| XXV | | | | | | | | |
| MF 270 | 10' | N.D. | 10' | $0.6 \times 10^{-7}$ | 10' | N.D. | 10' | N.D. |
| XVI | | | | | | | | |
| MF 271 | 10' | N.D. | 10' | $0.5 \times 10^{-7}$ | 10' | N.D. | 10' | N.D. |
| XXXI | | | | | | | | |
| MF 27 | 10' | N.D. | 10' | $0.3 \times 10^{-7}$ | 10' | N.D. | 10' | N.D. |
| XV | | | | | | | | |
| MF 47 | 10' | N.D. | 10' | $1.7 \times 10^{-8}$ | 10' | N.D. | 10' | N.D. |
| XVIII | | | | | | | | |
| MF 250 | 10' | N.D. | 10' | $0.3 \times 10^{-7}$ | 10' | N.D. | 10' | N.D. |
| XXXV | | | | | | | | |
| MF 252 | 10' | N.D. | 10' | $0.3 \times 10^{-7}$ | 10' | N.D. | 10' | N.D. |
| XXVII | | | | | | | | |
| MF 248 | 10' | N.D. | 10' | $1.9 \times 10^{-8}$ | 10' | N.D. | 10' | N.D. |
| XXXIII | | | | | | | | |
| MF 249 | 10' | N.D. | 10' | $0.5 \times 10^{-7}$ | 10' | N.D. | 10' | N.D. |
| XXXIV | | | | | | | | |
| MF 239 | 10' | N.D. | 10' | $0.5 \times 10^{-7}$ | 10' | N.D. | 10' | N.D. |
| VIII | | | | | | | | |
| MF 237 | 10' | $3.4 \times 10^{-7}$ | 10' | $1.1 \times 10^{-7}$ | 10' | N.D. | 10' | N.D. |
| XVII | 30' | $1.9 \times 10^{-7}$ | 30' | $0.7 \times 10^{-7}$ | | | | |
| | 60' | $1.2 \times 10^{-7}$ | 60' | $0.3 \times 10^{-7}$ | | | | |
| MF 254 | 10' | N.D. | 10' | $0.5 \times 10^{-7}$ | 10' | N.D. | 10' | N.D. |
| XIX | | | | | | | | |
| MF 256 | 10' | N.D. | 10' | $0.8 \times 10^{-7}$ | 10' | N.D. | 10' | N.D. |
| XXVIII | | | | | | | | |
| MF 257 | 10' | N.D. | 10' | $0.3 \times 10^{-7}$ | 10' | N.D. | 10' | N.D. |
| XXIX | | | | | | | | |
| MF 258 | 10' | N.D. | 10' | $1.0 \times 10^{-6}$ | 10' | N.D. | 10' | N.D. |
| XXX | | | | | | | | |
| MF 265 | 10' | N.D. | 10' | $0.8 \times 10^{-7}$ | 10' | N.D. | 10' | N.D. |
| IX | | | | | | | | | ps Legend:
AChE E.eel: acetylcholinesterase from electric eel
AChE nRBC: acetylcholinesterase from human red blood cells
AChE rat brain: acetylcholinesterase from homogenate of in toto rat brain
BuChE hserum: butyrylcholinesterase from human serum
N.D.: not determined
t: contact time (minutes)
IC$_{50}$ M: median inhibitory molar concentration The results reported in Table 2 demonstrate that the inhibition of acetylcholinesterase activity by the claimed products is high. Particularly active against human red blood cells acetylcholinesterase are the compounds where R stands for morpholine where n ranges from 8 to 12 (Ex.7), (V), (VI)
2,6-dimethylmorpholine where n=8 (Ex.17), (Ex.18)
thiomorpholine where n=8 (VIII)
methylpiperazine where n=8 (Ex.13), n=10 (XXII), n=12 (XXI)
ethylpiperazine where n=8 (XIII)
propylpiperazine where n=8 (XIV)
butylpiperazine where n=8 (XV)
acetylpiperazine where n=10 (X)
benzylpiperazine where n=8 (XX)
piperidine where n=8 (Ex.15), n=10 (XXXIII), n=12 (XXXIV)
1,4-dioxa-8-azaspirodecane where n=8 (IX)
pyrrolidine where n=8 (Ex.14) and n=10 (XXVII)
diethylamine where n=8 (XVII), n=10 (XVIII), n=12 (XIX)

dipropylamine where n=8 (XXVIII), n=10 (XXIX)
methylbenzylamine where n=8 (XXXII)
bis(methoxy)ethylamine where n=8 (XXXI).

Compared with the compounds of this invention, the compound of Example 30 (EPA 0253372) exhibits a much lower activity.

In the tests with BuChE hserum, the compounds of the present invention gave slightly lower results than heptastigmine and physostigmine: this proves that the claimed products—especially compared with heptastigmine—are mope selective toward acetylcholinesterase.

Furthermore, the claimed compounds—compared with those already known—produce much lesser side effects, as proved by the tests conducted for their determination. Table 3 shows the results obtained by acute toxicity tests on rats.

The aforementioned properties make the claimed compounds, i.e. the compounds as per formula (I) and their salts with pharmacologically acceptable acids, suitable for the treatment of all diseases characterized by acetylcholine deficiency, such as for example the diseases connected with memory dysfunctions (Alzheimer's disease), or of ischaemic type brain diseases.

For that reason, pharmaceutical compositions containing said compounds in efficacious quantities mixed with pharmacologically acceptable diluents and excipients were prepared.

The invention also contemplates the method of treatment of human diseases characterized by acetylcholine deficiency, consisting of the administration of a pharmachologically efficacious quantity of said compounds by opal or parenteral route.

The therapy envisages a daily dose of compound (I) of 5 to 150 mg for oral administration and of 2.5 to 75 mg for parenteral administration.

TABLE 3

| Acute toxicity to rats | | |
|---|---|---|
| | | DL$_{50}$ os (mg/kg) |
| ESERINE | — | 4.5 |
| MF 239 | VIII | 23.8 |
| MF 231 | VI | 40 |
| MF 230 | Ex. 13 | 27.7 |
| MF 217 | Ex. 7 | 23 |
| MF 256 | XXVIII | 18.28 |
| MF 247 | XVIII | 14.1 |
| MF 248 | XXXIII | 15.3 |
| MF 268 | Ex. 17 | 56 |

We claim:

1. Process for the preparation of aminoalkylcarbamic esters of eseroline having general formula (I)

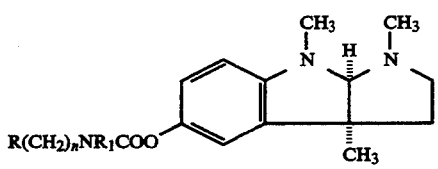

where n is an integer from 2 to 20 (atoms); R1 may be H, methyl, ethyl, propyl, and isopropyl; and R is an amine selected out of the group consisting of

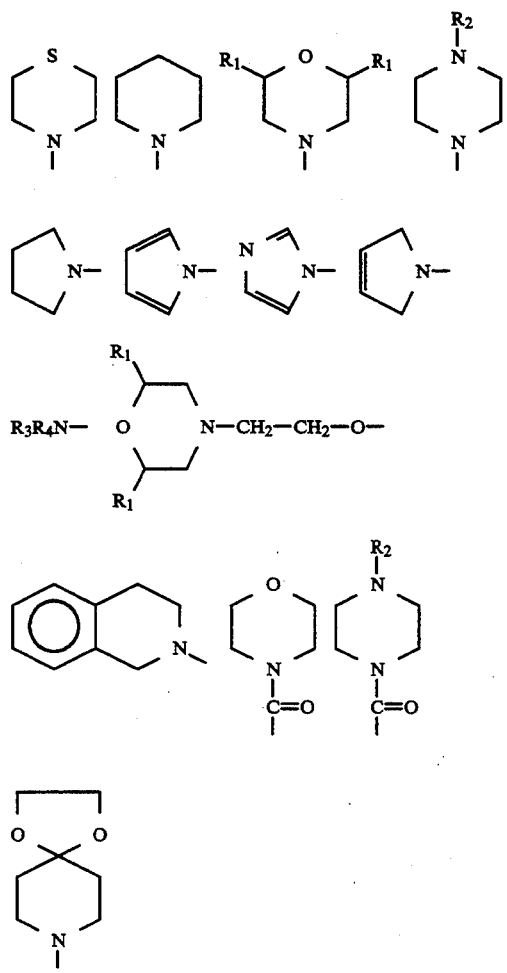

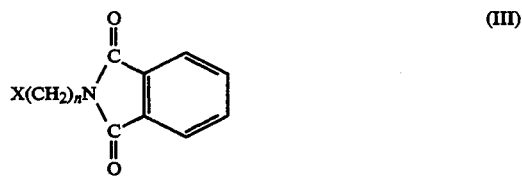

where R2 is linear or branched C$_1$–C$_4$ alkyl, or acyl or benzyl; R3 and R4 are linear or branched C$_1$–C$_4$ alkyls, or benzyl or methoxyethyl, methoxypropyl, methoxybutyl, wherein a compound RH, where R is as defined above, is caused to react with Ω-haloalkylphthalimide of formula (III)

$$X(CH_2)_nN\begin{array}{c}C=O\\ \\C=O\end{array}\bigcirc \quad (III)$$

where X is selected out of the group consisting of F, Cl, Br, and I;

b) the phthalic group of the obtained compound is removed by hydrazinolysis to give a primary amino derivative as per formula (IV)

$$R(CH_2)_nNH_2 \quad (IV)$$

c) carbonyl diimidazole is caused to react with eseroline and then with the aforesaid amino derivative (IV) to obtain compounds (I), where R1=H, the amino derivative (IV) being alkylated to give the corresponding secondary amino derivative before proceeding to step c) to form compounds (I), where R1 stands for said alkyl group.

2. The process according to claim 1 wherein step a) is carried out in a solvent selected among ethyl ether, acetonitrile and tetrahydrofuran, at room temperature and with a molar ratio of RH to (III) ranging between 3:1 and 1:1.

3. The process according to claim 1 wherein step b) is carried out in methanol, the mixture being heated to reflux.

4. The process according to claim 1 wherein the reaction with eseroline (step c) is carried out in a solvent selected out of methylene chloride, toluene, benzene, xylene and DMF at room temperature and with a molar ratio of carbonyl diimidazole to eseroline between 3:1 and 1:1.

5. The process according to claim 1 wherein the reaction with amino derivative (IV) (step c) is carried out at room temperature and with a molar ratio of (IV) to carbonyl diimidazole between 2:1 and 1:1.

6. The process according to claim 1 wherein the alkylation of amino derivative (IV) is carried out in the presence of alkylating substances selected out of the group consisting of dimethylsulphate and ethyl, propyl and isopropyl halides.

7. The process according to claim 1 wherein said alkylation of amino derivative (IV) is carried out by monobenzylation with benzyl bromide followed by treatment with a halide selected out of the group consisting of ethyl, propyl and isopropyl halides, and subsequent debenzylation by hydrogenolysis.

* * * * *